(12) United States Patent
Kumar et al.

(10) Patent No.: US 11,642,351 B2
(45) Date of Patent: *May 9, 2023

(54) ESLICARBAZEPINE SUSPENSION

(71) Applicant: Jubilant Generics Limited, Noida (IN)

(72) Inventors: Dinesh Kumar, Noida (IN); Saurabh Srivastava, Noida (IN); Indranil Nandi, Yardley, PA (US); Rakesh K. Singh, Noida (IN); Amit Jha, Noida (IN); Kamal S. Mehta, Noida (IN)

(73) Assignee: Jubilant Generics Limited

( * ) Notice: Subject to any disclaimer, the term of this patent is extended or adjusted under 35 U.S.C. 154(b) by 56 days.

This patent is subject to a terminal disclaimer.

(21) Appl. No.: 16/827,534

(22) Filed: Mar. 23, 2020

(65) Prior Publication Data

US 2020/0222420 A1   Jul. 16, 2020

Related U.S. Application Data

(63) Continuation-in-part of application No. PCT/IB2018/057400, filed on Sep. 25, 2018.

(51) Int. Cl.
| | |
|---|---|
| *A61K 31/55* | (2006.01) |
| *A61K 47/26* | (2006.01) |
| *A61K 47/34* | (2017.01) |
| *A61K 47/38* | (2006.01) |
| *A61K 9/00* | (2006.01) |
| *A61K 9/16* | (2006.01) |

(52) U.S. Cl.
CPC .............. *A61K 31/55* (2013.01); *A61K 47/26* (2013.01); *A61K 47/34* (2013.01); *A61K 47/38* (2013.01); *A61K 9/0053* (2013.01); *A61K 9/16* (2013.01)

(58) Field of Classification Search
CPC ........ A61K 31/55; A61K 47/26; A61K 47/34; A61K 47/38
See application file for complete search history.

(56) References Cited

U.S. PATENT DOCUMENTS 7,175,855 B1 * 2/2007 Arenson ............... A61K 9/0095
514/249
2014/0294972 A1 * 10/2014 White ..................... A61K 9/10
514/263.3

FOREIGN PATENT DOCUMENTS

WO    WO 2011/031176    *  3/2011

* cited by examiner

*Primary Examiner* — Genevieve S Alley
(74) *Attorney, Agent, or Firm* — William D. Hare, Esq.; McNeely, Hare & War, LLP

(57) ABSTRACT

The present invention relates to orally administered liquid pharmaceutical compositions of eslicarbazepine. The liquid compositions are in the form of ready to use suspension and suspension powder for reconstitution. It also relates to the processes for the preparation of said liquid compositions. The present invention provides liquid compositions of eslicarbazepine with desired technical attributes such as release profile and pH. The prepared compositions are useful in patients having difficulties in swallowing tablets and provide physician with providing a more convenient and less cumbersome posology.

19 Claims, No Drawings

ESLICARBAZEPINE SUSPENSION

This is a continuation-in-part of International Application PCT/IN2018/057400, with a filing date of Sep. 25, 2018, which claims priority to Indian Application No. 201711033833, with a filing date of Sep. 25, 2017.

FIELD OF THE INVENTION

The present invention relates to orally administered liquid pharmaceutical compositions of eslicarbazepine. The liquid compositions are in the form of ready to use suspension and suspension powder for reconstitution. It also relates to the processes for the preparation of said liquid compositions.

BACKGROUND OF THE INVENTION

Eslicarbazepine acetate is an anticonvulsant drug. It is chemically known as (S)-IO-acetoxy-10, 11-dihydro-5H-dibenz [b,f]azepine-5-carboxamide.

Eslicarbazepine is marketed in the United States as an immediate release tablet in of 200 mg, 400 mg, 600 mg and 800 mg strengths under the brand name APTIOM® (Eslicarbazepine acetate Oral Tablets 200 mg, 400 mg, 600 mg and 800 mg) by Sunovion Pharmaceuticals. The marketed solid dosage form of eslicarbazepine are indicated for the treatment of partial onset seizures.

The tablet dosage form of eslicarbazepine has large tablet size and weight. Difficulty in swallowing large tablets and capsules is a problem for many patients and can lead to a variety of adverse events as well as induce significant non-compliance with the prescribed treatment regimens. Adolescents, children, and the elderly are particularly vulnerable population groups that are more likely than adults to experience difficulty in swallowing large tablets or capsules. The liquid dosage forms formulation design with an objective to minimize swallowing difficulties is likely to improve patient compliance by reducing dysphagia-related adverse events due to large tablet size and accordingly providing a more convenient and less cumbersome posology U.S. Publication No. 2013/0040939 discloses oral suspension formulation of eslicarbazepine comprising xanthan gum as a suspending agent and polyoxyethylene stearate as a wetting agent.

There exists a need in the art to provide alternate liquid compositions of eslicarbazepine which are stable, provides ease of administration, dose adjustment, and enhanced patient compliance. The inventors of the present invention prepared suspension and suspension powder for reconstitution convenient for administration by pediatric and geriatric patients, easy to manufacture, functionally reproducible, and provide ease of dose adjustment. Further, the liquid compositions exhibit desirable technical attributes

OBJECTS AND SUMMARY OF THE INVENTION

It is a principal object of the present invention to provide a stable immediate release oral liquid pharmaceutical composition comprising an anticonvulsant drug with one or more pharmaceutically acceptable excipient and process for its preparation.

It is another object of the present invention to provide a suspension comprising eslicarbazepine or its pharmaceutically acceptable esters, salts, solvates, polymorphs, enantiomers or mixtures thereof with one or more pharmaceutically acceptable excipients and/or carrier and process for their preparation.

It is another object of the present invention to provide a suspension powder for reconstitution comprising eslicarbazepine or its pharmaceutically acceptable esters, salts, solvates, polymorphs, enantiomers or mixtures thereof with one or more pharmaceutically acceptable excipients and/or carrier and process for their preparation.

It is another object of the present invention to provide an oral liquid pharmaceutical composition in the form of a suspension comprising eslicarbazepine or its pharmaceutically acceptable esters, salts, solvates, polymorphs, enantiomers or mixtures thereof with one or more pharmaceutically acceptable excipients and/or carrier wherein the pharmaceutically acceptable excipient is selected from the group comprising of suspending agent, antioxidant, anticaking agent, antifoaming agent, pH adjusting agent, coloring agent, sweetening agent, flavouring agent, solubilizer/wetting agent, buffer, diluent, preservative and mixtures thereof. The suspension is in the form of ready to use suspension and suspension powder for reconstitution.

The following embodiments further describe the objects of the present invention in accordance with the best mode of practice, however, disclosed invention is not restricted to the particular embodiments hereinafter described.

In accordance with one embodiment of the present invention, there is provided an immediate release oral pharmaceutical suspension dosage form of eslicarbazepine comprising:
  a) eslicarbazepine or its pharmaceutically acceptable salt, ester, hydrate or polymorph thereof from about 0.1-40% w/w;
  b) a suspending agent from about 0.05-10% w/w; and
  c) a surfactant from 0-7% w/w; wherein the dosage form is free from xanthan gum and/or polyoxyethylene stearate.

In accordance with another embodiment of the present invention, there is provided an immediate release oral pharmaceutical suspension dosage form of eslicarbazepine comprising:
  a) eslicarbazepine or its pharmaceutically acceptable salt, ester, hydrate or polymorph thereof from about 0.1-40% w/w:
  b) a suspending agent from about 0.05-10% w/w; and
  c) a surfactant from 0-7% w/w; wherein the pH of the suspension is from 3-8 and the dosage form is free from xanthan gum and/or polyoxyethylene stearate.

In accordance with another embodiment of the present invention, there is provided an immediate release oral pharmaceutical suspension dosage form of eslicarbazepine comprising:
  a) eslicarbazepine or its pharmaceutically acceptable salt, ester, hydrate or polymorph thereof from about 0.1-40% w/w;
  b) a suspending agent from about 0.05-10% w/w; and
  c) a surfactant from 0-7% w/w; and
  d) a pharmaceutically acceptable liquid carrier; wherein the dosage form is free from xanthan gum and/or polyoxyethylene stearate.

In accordance with another embodiment of the present invention, there is provided an immediate release oral pharmaceutical suspension dosage form of eslicarbazepine comprising:
  a) eslicarbazepine or its pharmaceutically acceptable salt, ester, hydrate or polymorph thereof from about 0.1-40% w/w;
  b) a suspending agent from about 0.05-10% w/w; and
  c) a surfactant from 0-7% w/w;

wherein the dosage form is free from xanthan gum and/or polyoxyethylene stearate and exhibits an in-vitro dissolution rate of more than 65% of drug release within 20 minutes, when said dosage form is placed in a dissolution vessel filled with 1000 ml of acetate buffer, pH 4.5 maintained at 37+0.5° C. and stirred at a paddle speed of 100 rpm using a USP Type II (paddle) apparatus.

In accordance with another embodiment of the present invention, the immediate release oral pharmaceutical suspension dosage form of eslicarbazepine is a ready to use suspension or suspension powder for reconstitution.

In accordance with another embodiment of the present invention, the immediate release oral pharmaceutical suspension dosage form of eslicarbazepine has eslicarbazepine in an amount from about 0.1 mg/mL to about 200 mg/mL and viscosity from about 700-1200 cps.

In accordance with another embodiment of the present invention, there is provided an immediate release oral pharmaceutical suspension dosage form of eslicarbazepine or its pharmaceutically acceptable salt, ester, hydrate or polymorph thereof with one or more pharmaceutically acceptable excipients comprising:
  a. a suspending agent;
  b. a preservative:
  c. optionally a surfactant;
  d. optionally an antioxidant:
  e. pH adjusting agent in sufficient amounts to maintain the pH of the composition in the range of about 3.0 to about 8.0; and/or pharmaceutically acceptable liquid carrier; wherein the composition is free of xanthan gum and/or polyoxyethylene stearate.

In accordance with another embodiment of the present invention, there is provided an immediate release oral pharmaceutical suspension dosage form of eslicarbazepine or its pharmaceutically acceptable salt, ester, hydrate or polymorph thereof with one or more pharmaceutically acceptable excipients comprising:
  a. a suspending agent:
  b. a diluent;
  c. a preservative;
  d. optionally an antioxidant;
  e. pH adjusting agent in sufficient amounts to maintain the pH of the composition in the range of about 3.0 to about 8.0; and/or pharmaceutically acceptable liquid carrier, wherein the suspending agent is selected from the group comprising gellan gum, cellulose and its derivatives, a mixture of carboxymethylcellulose and microcrystalline cellulose, propylene glycol alginate, and combinations thereof.

In accordance with another embodiment of the present invention, there is provided an immediate release oral pharmaceutical suspension dosage form of eslicarbazepine or its pharmaceutically acceptable salt, ester, hydrate or polymorph thereof with one or more pharmaceutically acceptable excipients comprising:
  a. a suspending agent;
  b. a surfactant;
  c. a preservative;
  d. optionally an antioxidant:
  e. pH adjusting agent in sufficient amounts to maintain the pH of the composition in the range of about 3.0 to about 8.0; and/or pharmaceutically acceptable liquid carrier,
  wherein the surfactant is selected from the group comprising non-ionic surfactants, anionic, cationic or zwitterionic surfactants with the proviso that surfactant is not polyoxyethylene stearate.

In accordance with another embodiment of the present invention, there is provided an immediate release oral pharmaceutical suspension dosage form of eslicarbazepine or its pharmaceutically acceptable salt, ester, hydrate or polymorph thereof with one or more pharmaceutically acceptable excipients comprising eslicarbazepine from about 0.1 mg/mL to about 200 mg/mL, wherein the pH of the composition is from 3-8.

In accordance with another embodiment of the present invention, there is provided an immediate release oral pharmaceutical suspension dosage form of eslicarbazepine or its pharmaceutically acceptable salt, ester, hydrate or polymorph thereof with one or more pharmaceutically acceptable excipients comprising eslicarbazepine from about 0.1 mg/mL to about 200 mg/mL, wherein the pH of the composition is from 3-8 and viscosity from 700-1200 cps.

In accordance with a one embodiment of the present invention, there is provided a suspension powder for reconstitution comprising eslicarbazepine or its pharmaceutically acceptable esters, salts, solvates, polymorphs, enantiomers or mixtures thereof and at least one or more pharmaceutically acceptable excipient selected from the group comprising a suspending agent/thickening agent/viscosity agent, antioxidant, anticaking agent, antifoaming agent, pH adjusting agent, coloring agent, sweetening agent, flavouring agent, surfactant/wetting agent, buffer, diluent and preservative.

In accordance with one embodiment of the present invention, there is provided a ready to use stable liquid suspension comprising eslicarbazepine or its pharmaceutically acceptable esters, salts, solvates, polymorphs, enantiomers or mixtures thereof and at least one or more pharmaceutically acceptable excipient and/or carrier wherein the pharmaceutically acceptable excipient is selected from the group comprising a thickening agent/viscosity agent, antioxidant, anticaking agent, antifoaming agent, pH adjusting agent, coloring agent, sweetening agent, flavouring agent, surfactant/wetting agent, buffer, diluent, and preservative.

In accordance with another embodiment of the present invention, there is provided dry powder for suspension compositions suitable for use as a liquid suspension for children or elderly patients. The compositions include eslicarbazepine or its pharmaceutically acceptable esters, salts, solvates, polymorphs, enantiomers or mixtures thereof and pharmaceutically acceptable excipients selected from the group consisting of suspending agents, coating agents, preservatives, flavouring agents, sweeteners, lubricants, surfactants, buffering agents, and diluents.

In accordance with still another embodiment of the present invention, there is provided a process for the preparation of a stable pharmaceutical composition in the form of a suspension comprising eslicarbazepine or its pharmaceutically acceptable esters, salts, solvates, polymorphs, enantiomers or mixtures thereof.

In accordance with still another embodiment of the present invention, there is provided a process for the preparation of a stable pharmaceutical composition in the form of a suspension comprising eslicarbazepine or its pharmaceutically acceptable esters, salts, solvates, polymorphs, enantiomers or mixtures thereof, wherein eslicarbazepine or its pharmaceutically acceptable esters, salts, solvates, polymorphs, enantiomers or mixtures thereof is in micronized form.

In accordance with still another embodiment of the present invention, there is provided a process for the preparation of a ready to use liquid suspension of eslicarbazepine or its pharmaceutically acceptable esters, salts, solvates, polymorphs, enantiomers or mixtures thereof, comprising combining various components using conventional equipment such as overhead stirrers, ultrasonifiers, mills, homogenizers. Many different orders of adding components can be employed.

In accordance with still another embodiment of the present invention, there is provided a process for the preparation of a dry powder for suspension composition of eslicarbazepine or its pharmaceutically acceptable esters, salts, solvates, polymorphs, enantiomers or mixtures thereof, which is suitable for suspension in water and/or water miscible suitable solvents to form an orally administrable product which comprises admixing eslicarbazepine granules with substantially dry pharmaceutically acceptable excipients selected from the group consisting of suspending agents/viscosity enhancers, coating agents, preservatives, flavouring agents, sweeteners, lubricants, wetting agents, surfactants, buffering agents, and diluents to form a dry admixture, and transferring the dry admixture to a sealable storage container.

In accordance with still another embodiment of the present invention, there is provided a stable pharmaceutical composition in the form of a suspension comprising eslicarbazepine or its pharmaceutically acceptable esters, salts, solvates, polymorphs, enantiomers or mixtures thereof, wherein the composition is substantially free from other polymorphic forms.

In accordance with still another embodiment of the present invention, there is provided a stable pharmaceutical composition in the form of a suspension comprising eslicarbazepine or its pharmaceutically acceptable esters, salts, solvates, polymorphs, enantiomers or mixtures thereof, wherein eslicarbazepine has a particle size distribution D less than about 200 µm. In accordance with still another embodiment of the present invention, there is provided a stable pharmaceutical composition in the form of a suspension comprising eslicarbazepine or its pharmaceutically acceptable esters, salts, solvates, polymorphs, enantiomers or mixtures thereof, in an amount of about 0.01% to about 90% by weight wherein, the composition exhibits desirable technical attributes like pourability, viscosity, dissolution, stability, re-suspendability and re-dispersibility and a process for preparing the same.

In accordance with still another embodiment of the present invention, there is provided a stable pharmaceutical composition in the form of a suspension comprising eslicarbazepine or its pharmaceutically acceptable esters, salts, solvates, polymorphs, enantiomers or mixtures thereof, for the treatment of epilepsy, neuropathic pain, migraine, fibromyalgia, trigeminal neuralgia, bipolar disorders, attention disorders, anxiety disorders, affective disorders, and schizoaffective disorders, sensorimotor disorders, and vestibular disorders.

In accordance with still another embodiment of the present invention, there is provided a kit comprising: (a) an immediate release oral pharmaceutical suspension dosage form comprising eslicarbazepine or its salt thereof with one or more pharmaceutically acceptable excipients and/or carrier, (b) a dispensing and/or dosing syringe for administering the composition; and (c) optionally, instructions for preparation and use.

DETAILED DESCRIPTION OF THE INVENTION

The present invention can be more readily understood by following detailed description of the invention and study of the included examples.

As used herein, the term "composition or "formulation" or "dosage form", as in pharmaceutical composition, is intended to encompass a drug product comprising an anticonvulsant or anti-epileptic drug, preferably eslicarbazepine or its pharmaceutically acceptable salts, esters, solvates, polymorphs, enantiomers or mixtures thereof, and other inert ingredient(s) (pharmaceutically acceptable excipients). Such pharmaceutical compositions are synonymous with "formulation" and "dosage form". Pharmaceutical composition of the invention include, but is not limited to powder for suspension, oral suspension and the like.

As used herein, the term "ready to use suspension" means a pre-constituted suspension which can be administered as such. The "powder for suspension" or "dry suspension" needs to be reconstituted with a liquid carrier to form a suspension.

As used herein, the term "eslicarbazepine" is used in broad sense to include not only "eslicarbazepine" per se but also its pharmaceutically acceptable salts, solvates, hydrates, enantiomers, derivatives, isomers, polymorphs, prodrugs thereof, and also its various crystalline and amorphous forms. In particular, the salt of eslicarbazepine is eslicarbazepine acetate. The term "eslicarbazepine acetate" used in this specification means the S-isomer in substantially pure form, i.e. at least about 98% pure.

The term "excipient" means a pharmacologically inactive component such as a suspending agent/viscosity agent, anticaking agent, antifoaming agent, pH adjusting agent, antioxidant, sweetening agent, flavoring agent, surfactant/solubilizer/wetting agent, buffer, and preservative and the like. The excipients used in preparing the liquid pharmaceutical composition are safe and non-toxic. Reference to an excipient includes both one and more than one such excipient. Co-processed excipients are also covered under the scope of present invention. Combination of excipients performing the same function may also be used to achieve desired formulation characteristics.

As used herein, the term "about" means+approximately 20% of the indicated value, such that "about 10 percent" indicates approximately 08 to 12 percent.

As used in this specification, the singular forms "a", "an", and "the" include plural references unless the context clearly dictates otherwise. Thus, for example, a reference to "a process" includes one or more process, and/or steps of the type described herein and/or which will become apparent to those persons skilled in the art upon reading this disclosure and so forth.

The term "stable," as used herein, refers to chemical stability, wherein not more than 5% w/w of total related substances are formed on storage at 40° C. and 75% relative humidity (R.H.) or at 25° C. and 60% R.H. for a period of at least one month, particularly for a period of two months, and more particularly for a period of at least three months.

Unless otherwise stated the weight percentages expressed herein are based on the final weight of the composition or formulation.

The present invention is a stable pharmaceutical composition directed to ready to use oral liquid suspension or dry powder for suspension compositions suitable for use as a liquid suspension for administration to a subject in need thereof which comprises eslicarbazepine or its pharmaceutically acceptable salts.

In accordance with one embodiment of the present invention, there is provided a stable pharmaceutical composition in the form of a suspension comprising eslicarbazepine or its pharmaceutically acceptable salts with one or more pharmaceutically acceptable excipient and/or liquid carrier and process for its preparation.

Another embodiment of the present invention relates to an immediate release oral pharmaceutical suspension dosage form of eslicarbazepine or its pharmaceutically acceptable salt, ester, hydrate or polymorph thereof with one or more pharmaceutically acceptable excipients comprising:
 a. a suspending agent;
 b. a preservative;
 c. optionally a surfactant;
 d. optionally an antioxidant:
 e. pH adjusting agent in sufficient amounts to maintain the pH of the composition in the range of about 3.0 to about 8.0; and/or pharmaceutically acceptable liquid carrier.

In accordance another embodiment of present invention, there is provided a suspension comprising eslicarbazepine or its pharmaceutically acceptable salts and one or more pharmaceutically acceptable excipients and/or a liquid carrier, wherein the composition is free of xanthan gum.

In accordance another embodiment of present invention, there is provided a suspension comprising eslicarbazepine or its pharmaceutically acceptable salts and one or more pharmaceutically acceptable excipients and/or a liquid carrier, wherein the composition is free of polyoxyethylene stearate.

In accordance another embodiment of present invention, there is provided a stable suspension comprising eslicarbazepine or its pharmaceutically acceptable salts and one or more pharmaceutically acceptable excipients and/or a liquid carrier, wherein the composition is free of xanthan gum and polyoxyethylene stearate.

In accordance with another aspect of the present embodiment, there is provided a stable suspension comprising eslicarbazepine or its pharmaceutically acceptable salts, wherein the suspending agent is selected from gellan gum, sodium carboxymethylcellulose, a mixture of carboxymethylcellulose and microcrystalline cellulose, propylene glycol alginate and combinations thereof.

In accordance with another embodiment of the present invention, sucrose has a particle size such that not less than 90% particles are below 200 µm. In particular, sucrose has a particle size such that not less than 90% particles are below 100 µm. This helps in achieving improved uniformity of the drug in the mixture.

In accordance with other embodiment of the present invention, there is provided a stable suspension comprising about 0.01% to about 90% by weight of eslicarbazepine or its pharmaceutically acceptable esters, salts, solvates, polymorphs, enantiomers or mixtures thereof, preferably in the range of about 0.1% to about 40% by weight on the basis of the total weight of the composition.

In accordance with other embodiment of the present invention, there is provided a stable suspension comprising eslicarbazepine or its pharmaceutically acceptable salts, wherein the amount of eslicarbazepine in the suspension ranges from about 0.1 mg/mL to about 400 mg/mL. The amount of eslicarbazepine in the suspension ranges preferably from about 0.5 mg/mL to 300 mg/mL, preferably from about 0.5 mg/mL to 200 mg/mL, preferably from about 0.5 mg/mL to 100 mg/mL. More preferably the amount of eslicarbazepine in the suspension ranges from about 0.5 mg/mL to 75 mg/mL.

In accordance with one aspect of the present embodiment, there is provided a stable suspension comprising eslicarbazepine or its pharmaceutically acceptable salts, wherein the amount of eslicarbazepine in suspension is 1 mg/mL, 2 mg/5 mL, 5 mg/5 mL, 25 mg/5 mL, 50 mg/5 mL, 100 mg/5 mL and 250 mg/5 mL, 5 mg/mL, 25 mg/mL, 50 mg/mL, 100 mg/mL and 250 mg/mL.

In accordance with other embodiment of the present invention, there is provided a stable suspension comprising eslicarbazepine or its pharmaceutically acceptable salts, wherein the pH of suspension is in range of about 3-9. Preferably, the pH is in a range of about 3-8. In accordance with other embodiment of the present invention, there is provided a stable suspension comprising eslicarbazepine or its pharmaceutically acceptable salts, wherein the suspension is a liquid suspension packaged in a bottle.

In accordance with yet another embodiment of the present invention, there is provided a stable suspension comprising eslicarbazepine or its pharmaceutically acceptable salts, wherein the suspension is a powder for suspension packaged in a bottle or sachets.

According to another embodiment of the present invention, eslicarbazepine has a particle size distribution $D_{90}$ less than about 200 µm. Eslicarbazepine has a particle size distribution $D_{90}$ between 5 µm and 200 µm. Eslicarbazepine has a particle size distribution particularly $D_{90}$ between 5 µm and 175 µm, particularly $D_{90}$ between 5 µm and 150 µm, particularly $D_{90}$ between 5 µm and 125 µm, particularly $D_{90}$ between 5 µm and 100 µm and particularly $D_{90}$ between 5 µm and 75 µm.

In accordance with one embodiment of the present invention, there is provided a process for preparation of a stable suspension comprising eslicarbazepine or its pharmaceutically acceptable salts and one or more pharmaceutically acceptable excipients and/or a liquid carrier, wherein process utilized is blending, dry granulation, wet granulation, spheronization extrusion process, hot melt extrusion process, homogenization or the like.

In accordance with one embodiment of the present invention, there is provided a process for preparation of a ready to use suspension comprising eslicarbazepine or its pharmaceutically acceptable salts and one or more pharmaceutically acceptable excipients and/or a liquid carrier, wherein process comprises the following steps:
 (i) dissolving/dispersing one or more pharmaceutically acceptable excipients in a portion of water:
 (ii) dispersing eslicarbazepine in the solution of step (i) to form a dispersion
 (iii) mixing suspending agent in another portion of water;
 (iv) adding the mixture of step (iii) to the dispersion of step (ii); and
 (v) optionally adding one or more pharmaceutically acceptable excipients to the dispersion of step (iv); and
 (vi) optionally homogenizing the mixture of step (iv) to form a suspension.

In accordance with other embodiment of the present invention, there is provided a process for preparation of a powder for suspension comprising eslicarbazepine or its pharmaceutically acceptable salts and one or more pharmaceutically acceptable excipients and/or a liquid carrier, wherein process comprises the following steps:
 (i) mixing eslicarbazepine with one or more pharmaceutically acceptable excipients:
 (ii) granulating the mixture of step (i) using a solvent;
 (iii) drying the granulated mixture of step (ii);
 (iv) milling the mixture of step (iii) to form granules; and
 (v) mixing the granules of step (iv) optionally with one or pharmaceutically acceptable excipients to form the suspension powder for reconstitution.

In accordance with other embodiment of the present invention, there is provided a process for preparation of a suspension powder for reconstitution comprising eslicarbazepine or its pharmaceutically acceptable salts and one or more pharmaceutically acceptable excipients and/or a liquid carrier, wherein process comprises the following steps:

(i) mixing eslicarbazepine with one or more pharmaceutically acceptable excipients:

(ii) compacting the mixture of step (i) to form slugs;

(iii) milling the slugs of step (ii) to form granules; and (v) mixing the granules of step (iii) optionally with one or pharmaceutically acceptable excipients to form the suspension powder for reconstitution.

In accordance with other embodiment of the present invention, there is provided a process for preparation of a suspension powder for reconstitution comprising eslicarbazepine or its pharmaceutically acceptable salts and one or more pharmaceutically acceptable excipients and/or a liquid carrier, wherein process comprises the following steps:

(i) mixing eslicarbazepine with one or more pharmaceutically acceptable excipients; and (ii) optionally lubricating the mixture of step (i) to form the suspension powder for reconstitution.

Powder/granules for oral suspension can be reconstituted using water or powder/granules for oral suspension can be administered by sprinkling the powder/granules on one teaspoonful of applesauce or empty granules into a small cup or teaspoon containing one teaspoon of apple juice.

The suspension of the present invention provides advantages such as absence of lumps even after long storage when the composition is shaken as well as good pourability. The suspension of the invention has good physical stability properties such as low level of sedimentation (reduced or no caking) and easy re-dispersion on agitation. Moreover, it provides dose uniformity during each administration.

In accordance with another embodiment of the present invention, there is provided a ready to use liquid suspension comprising eslicarbazepine or its pharmaceutically acceptable esters, salts, solvates, polymorphs, enantiomers or mixtures thereof and at least one or more pharmaceutically acceptable excipient and/or a liquid carrier comprising suspending agent, antioxidant, anticaking agent, antifoaming agent, pH adjusting agent, sweetening agent, flavouring agent, surfactant/wetting agent, buffer, and preservative wherein, the suspension is easily dispersible or re-suspendible in a pharmaceutically acceptable liquid carrier including aqueous and/or non-aqueous carrier.

In accordance with still another embodiment of the present invention, there is provided a stable suspension comprising eslicarbazepine or its pharmaceutically acceptable esters, salts, solvates, polymorphs, enantiomers or mixtures thereof, wherein the composition is substantially free from other polymorphic forms.

In accordance with still another embodiment of the present invention, there is provided a suspension comprising eslicarbazepine or its pharmaceutically acceptable esters, salts, solvates, polymorphs, enantiomers or mixtures thereof in an amount of about 0.01% to about 90% by weight wherein, the composition exhibits desirable technical attributes like pourability, viscosity, dissolution, stability, re-suspendability and re-dispersibility.

In accordance with still another embodiment of the present invention, there is provided a kit comprising:

(a) an immediate release oral pharmaceutical suspension dosage form comprising eslicarbazepine or its salt thereof with one or more pharmaceutically acceptable excipients and/or carrier, (b) a dispensing and/or dosing syringe for administering the composition, and (c) optionally, instructions for preparation and use.

In accordance with still another embodiment of the present invention, there is provided a kit comprising:

(a) an immediate release oral pharmaceutical suspension dosage form comprising eslicarbazepine or its salt thereof with one or more pharmaceutically acceptable excipients and/or carrier, (b) a dispensing and/or dosing syringe or a measuring cup for administering the composition, and (c) optionally, instructions for preparation and use.

In accordance with still another embodiment of the present invention, there is provided a kit comprising:

(a) an immediate release oral pharmaceutical suspension dosage form comprising eslicarbazepine or its salt thereof with one or more pharmaceutically acceptable excipients and/or carrier, (b) a measuring cup for administering the composition, and (c) optionally, instructions for preparation and use.

In another embodiment the liquid composition of the present invention includes particle size of eslicarbazepine or its pharmaceutically acceptable esters, salts, solvates, polymorphs, enantiomers or mixtures thereof, having a particle size distribution such that $D_{90}$ is less than about 200 μm, $D_{50}$ is less than about 100 μm and $D_{10}$ is less than about 50 μm. Particularly, $D_{50}$ is between about 5 μm to about 100 μm. The particle size of eslicarbazepine can be measured by suitable techniques such as Laser light scattering (e.g. Malvern Light Scattering), Coulter counter, microscopy, Fraunhofer diffraction and any other technique known in the art.

In another embodiment of the present invention there is provided a suspension powder for reconstitution comprising eslicarbazepine or its pharmaceutically acceptable esters, salts, solvates, polymorphs, enantiomers or mixtures thereof, present in an amount of more than 0.01% by weight based on the total weight of the composition with one or more pharmaceutically acceptable excipient and/or a liquid carrier such as suspending agent, antioxidant, anticaking agent, antifoaming agent, pH adjusting agent, sweetening agent, flavouring agent, solubilizer/wetting agent, buffer, and preservative, aqueous or nonaqueous carrier and the like.

Carrier/vehicle/solvent used in the suspension of the present invention include aqueous and non-aqueous carrier but are not limited to water, alcohol, polyethylene glycol, propylene glycol or glycerin buffers, oil, or combinations thereof. Oils include peanut oil, soy bean oil, corn oil, sesame oil, cottonseed oil, acetylated glycerides, ethyl oleate, mineral oil, fatty acid esters, mono- or di-fatty acid esters of polyethylene glycols, or glyceryl mono-oleate. Particularly, the suspensions are aqueous based. By "aqueous carrier" is meant a suspension comprising water, or a combination of water and a water-miscible organic solvent or solvents. Water-miscible solvents include but are not limited to propylene glycol, polyethylene glycol and ethanol. By "non-aqueous carrier" is meant a suspension in which the carrier does not include water. The carrier can also include one more pharmaceutically acceptable excipients which can be in dissolved or dispersed form. The carrier is present in an amount from about 30 w/w % to about 95 w/w %, particularly from about 50 w/w % to about 95 w/w %.

The viscosity agent/suspending agent enhances the physical stability of the composition by sufficiently increasing the viscosity so as to retard the settling rate, yet allowing adequate pourability. They also allow the product to be easily resuspendable so that an appropriate dose can be delivered with minimal shaking. Suitable thickening agents/ viscosity agents/suspending agents are selected from the group comprising cellulose derivatives such as hydroxyethyl cellulose, hydroxypropyl cellulose, hydroxypropylmethyl cellulose, methylcellulose, carboxymethyl cellulose and its salts/derivatives e.g., carboxymethyl cellulose sodium, microcrystalline cellulose, and co-processed spray dried forms of microcrystalline cellulose and carboxymethyl cellulose sodium (such as AVICEL® RC-501, AVICEL® RC-581, AVICEL® RC-591, and AVICEL® CL-611); carbomers (such as those available under the trade name CARBOPOL®); gums such as locust bean gum, tragacanth gum, arabinogalactan gum, agar gum, gellan gum, guar gum, apricot gum, karaya gum, sterculia gum, acacia gum, gum arabic, and carrageenan; pectin; propylene glycol alginate, dextran; gelatin; polyethylene glycols; polyvinyl compounds such as polyvinyl acetate, polyvinyl alcohol, and polyvinyl pyrrolidone; sugar alcohols such as xylitol and mannitol; colloidal silica; maltodextrin, starch; and mixtures thereof. The liquid compositions of the present invention are free of xanthan gum. The suspending agents/viscosity agents are present in an amount of about 0.05% to about 20% w/w of the composition. Particularly, the viscosity agents are present in an amount of about 0.1% to about 10% w/w of the composition. More particularly, the viscosity agents are present in an amount of about 0.1% to about 5% w/w of the composition. Much more particularly, the viscosity agents are present in an amount of about 0.1% to about 3% w/w of the composition.

The suspension is easily pourable and when shaken has a viscosity in the range of 100 to 5000 cP at 25° C. Particularly, the viscosity is in the range of 100 to 2500 cP at 25° C. Particularly, the viscosity is in the range of 100 to 1500 cP at 25° C. More particularly, the viscosity is in the range of 700-1200 cps at 25° C.

The term "shaken" as used herein refers to shaken prior to use, e.g. by a patient, e.g. vigorously shaken, e.g. by hand, e.g. for 5 to 40 seconds.

The viscosity can be measured by using as suitable instrument such as Brookfield viscometer, Haake VT 550 viscometer at room temperature (25° C.).

Diluents or fillers are substances which usually provide bulk to the composition. Various useful fillers or diluents include, but are not limited to sucrose, sugar alcohols, sorbitol, xylitol, erythritol, starch, pregelatinized starch, calcium carbonate, calcium phosphate, dibasic anhydrous, calcium phosphate, dibasic dihydrate, calcium phosphate tribasic, calcium sulphate, cellulose powdered, silicified microcrystalline cellulose, cellulose acetate, lactose, magnesium carbonate, magnesium oxide, maltodextrin, mannitol, microcrystalline cellulose, polydextrose, sodium alginate, sodium chloride and or mixtures thereof. Preferably diluent used is sucrose. The diluent is present in an amount of 5 to 80% of the total composition.

The amount of surfactant or wetting agent should be sufficient to facilitate the dispersion of eslicarbazepine in the suspension. At the same time, it should provide improved wettability of the eslicarbazepine acetate. Suitable surfactant or wetting agents are selected from the group comprising non-ionic, anionic, cationic, or zwitterionic surfactants, and combinations thereof. Suitable examples of wetting agents are sodium lauryl sulphate; cetrimide; polyethylene glycols; polyglycerin fatty acid esters such as decaglyceryl monolaurate and decaglyceryl monomyristate; sorbitan fatty acid esters such as sorbitan monostearate; polyoxyethylene sorbitan fatty acid esters such as polyoxyethylene sorbitan monooleate; polyoxyethylene alkyl ether such as polyoxyethylene lauryl ether; polyoxyethylene castor oil; polyoxyethylene-polyoxypropylene block copolymers such as poloxamers (e.g. Poloxamer188); and combinations thereof. Particularly, surfactant or wetting agents are non-ionic. The liquid compositions of the present invention are free of polyoxyethylene stearate such as polyoxy 100 stearate (MYRJ® 59P) as wetting agent. The surfactant or wetting agents are present in an amount of about 0.01% to about 7% w/w of the composition. Particularly, the surfactant or wetting agents are present in an amount of about 0.01% to about 3% w/w, and more particularly from about 0.01% to about 1% w/w of the composition.

Various useful preservatives include, but are not limited to, parabens such as methylparaben, propylparaben, butyl paraben and their salts, sorbic acid, sodium sorbate, potassium sorbate, calcium sorbate, benzoic acid, sodium benzoate, potassium benzoate, calcium benzoate, methyl hydroxybenzoate, ethyl para-hydroxybenzoate, sodium ethyl para-hydroxybenzoate, sodium metabisulphite, chlorhexidine, diazolidinyl urea, sodium citrate, butylated hydroxyl toluene (BHT), butylated hydroxyl anisole (BHA), tocopherol, ethylenediamine tetraacetic acid, propyl gallate, quaternary compounds, e.g. benzalkonium chloride and cetylpyridinium chloride, phenyl ethyl alcohol and combinations thereof. In particular, the preservative is selected from benzoic acid and its salts and parabens. The preservative is present in an amount of about 0.001% w/w to about 3% w/w of the composition. Anticaking agent helps to improve the re-suspendability of the formulation. Various useful Anticaking agents include, but are not limited to, colloidal silica and/or colloidal silicon dioxide, calcium phosphate tribasic, magnesium oxide, magnesium silicate, calcium silicate and combinations thereof. The anticaking agents are present in an amount of about 0.1% to about 10% w/w of the composition. More particularly, the anticaking agents are present in an amount of about 0.5% to about 7% w/w of the composition.

Various useful antioxidants include, but are not limited to, ascorbic acid, tert-butylhydroquinone, sodium pyrosulfite, glutathione, sodium bisulfite, sodium sulfite, a-tocopherol, a-tocopherol acetate, monothioglycerol, cysteine, ascorbyl palmitate, acetylcysteine, dithiothreitol, sodium metabisulfite, thiourea, sodium thiosulfate, butylated hydroxy anisole (BHA), butylated hydroxytoluene (BHT) and propyl gallate.

Various useful sweetening agents include, but are not limited to, sugar or a sugar alcohol such as sucrose, dextrose, sucralose, sorbitol, fructose, mannitol and invert sugar and sugar substitutes such as saccharin sodium, aspartame. Sugar or a sugar alcohol can also act as filler. Preferably sweetening agent used is sodium saccharin.

Various useful flavoring agents, include, but are not limited to, flavors such as banana, lemon, orange, grape, lime and grapefruit, vanilla, bubble gum, and fruit essence, including apple, banana, pear, peach, strawberry, raspberry, cherry, plum, pineapple, apricot; synthetic flavor oils and flavoring aromatics and/or natural oils, extracts from plant leaves, flowers, fruits such as cinnamon oil, oil of wintergreen, peppermint oils, clove oil, citrus oil, bay oil, anise oil, eucalyptus, thyme oil, cedar leaf oil, oil of nutmeg, oil of sage, oil of bitter almonds, and cassia oil; maltol, ethyl vanillin, menthol, citric acid, fumaric acid, ethyl maltol, and tartaric acid and combinations thereof.

Various useful isotonizing agent include, but are not limited to, sodium chloride, mannitol, D-sorbitol, glucose, glycerin or the like.

Various useful pH adjusting agent or buffering agents include, but are not limited to, citrate buffers, phosphate buffers, or any other suitable buffer known in the art including monosodium dibasic phosphate, gluconic acid, lactic acid, citric acid, acetic acid, sodium gluconate, sodium lactate, sodium citrate, sodium acetate potassium citrate, sodium bicarbonate, potassium bicarbonate, sodium dihydrogen phosphate and potassium dihydrogen phosphate. Various useful taste masking agents include, but are not limited to, water soluble and/or insoluble polymeric excipient, water insoluble non-polymeric excipient, adsorbent, ion exchange resin, carbomer, alkali metal chlorides or an alkaline earth metal chloride or a derivative thereof.

Various useful antifoaming agents include, but are not limited to simethicone.

The pharmaceutical composition of the present invention can be packaged in a suitable pack/container such as amber colored polyethylene terephthalate (PET) bottle, glass bottle, high density polyethylene (HDPE) bottle, low density polyethylene (LDPE) bottle, polypropylene (PP) bottle, packets, pouches, sachets and the like. The glass or plastic bottle is provided with a child proof closure. The package can include a syringe, dosing syringe or dispensing syringe or measuring cup or any combination (marked in mL) for ease of dosing. The container(s) of the present invention may have a syringe adapted to be attached to the container. The syringe or cup as per the present invention can be of material such as polyethylene terephthalate (PET), glass, high density polyethylene (HDPE), low density polyethylene (LDPE), polypropylene (PP) or any other material known in the art.

The container such as bottle has a fill volume of, e.g., from about 50 mL to about 500 mL comprising eslicarbazepine suspension. Pack chosen are made of material which is non-reactive with the suspension and suspension powder for reconstitution. Containers for use in the storage of the oral suspensions may be used to administer a multiple dose of eslicarbazepine.

The liquid pharmaceutical composition of the present invention can be used for treatment of seizures.

The compositions of the present invention are for oral administration. The compositions may be taken in measured doses using a container, cup, straw, spoon, syringe, dispensing syringe, dosing syringe or any other suitable device. The compositions may be provided in liquid form, or in dry form (such as granule or powder or multiparticulate) to which water or liquid solvent or diluent is added to provide a liquid composition of this invention. Ingredients suitable for liquid compositions are known and such compositions may be made by methods known in the art. In an embodiment, the syringe, dispensing syringe or dosing syringe or combination thereof are used to transfer a predetermined amount of the composition comprising eslicarbazepine or its salt thereof, into the patient's mouth. In an embodiment, the measuring cup is used to measure the dose as per patient's requirement so that a precise dosage can be obtained for oral administration.

Suitable coloring agent are selected from the group comprising FD&C (Federal Food, Drug and Cosmetic Act) approved coloring agents; natural coloring agents; natural juice concentrates; pigments such as iron oxide, titanium dioxide, and zinc oxide; and combinations thereof.

The suspensions of the present invention are homogenous and deliver the desired dose of eslicarbazepine in every use without any risk of overdosing or underdosing. The compositions provide predictable eslicarbazepine release throughout the shelf life.

The invention may be further illustrated by the following examples, which are for illustrative purposes only and should not be construed as limiting the scope of the invention in any way.

EXAMPLES

Example 1—Ready to Use Suspension

| Ingredients | Quantity (% w/w) |
|---|---|
| Eslicarbazepine acetate | 6.7 |
| Sucrose | 26.8 |
| Sorbitol | 40.2 |
| Poloxamer 188 | 1.1 |
| Propylene glycol | 15.01 |
| Polysorbate 80 | 4.7 |
| Citric acid | 0.06 |
| Monosodium dibasic phosphate | 0.03 |
| Sodium saccharin | 0.08 |
| Methyl paraben | 0.16 |
| Propyl paraben | 0.11 |
| AVICEL® RC591 (Microcrystalline cellulose and sodium carboxymethylcellulose)/Sodium carboxymethylcellulose | 0.89 |
| Acesulfane potassium | 1.61 |
| Bubble gum flavor | 0.04 |
| Purified water | q.s. |

Procedure:

1. Polysorbate 80 and eslicarbazepine acetate were mixed.
2. Propylene glycol and Poloxamer 188 were added to step 1 and mixed.
3. Sodium saccharin, mono sodium dibasic phosphate anhydrous and citric acid were added to purified water to form a solution.
4. Methyl paraben and propyl paraben were added to propylene glycol to obtain a clear solution.
5. AVICEL® RC 591/sodium carboxymethylcellulose were added to water.
6. Solution of step 3 was added to step 2 and mixed.
7. Solution of step 4 was added to step 6 and mixed.
8. Dispersion of step 5 was added to step 7 and mixed.
9. Sucrose, sorbitol, acesulfame potassium, bubble gum flavor were added to water and mixed with mixture of step 8 and homogenized.

Examples 2-6—Suspension Powder for Reconstitution

| | Quantity (% w/w) | | | | |
|---|---|---|---|---|---|
| Example | 2 | 3 | 4 | 5 | 6 |
| Eslicarbazepine acetate | 12.50 | 12.50 | 12.50 | 12.50 | 12.50 |
| Sucrose | 86.30 | 79.60 | 79.53 | 78.72 | 78.48 |
| Polysorbate 80 | — | — | 0.08 | — | — |
| Citric acid | 0.11 | 0.11 | 0.11 | 0.11 | — |
| Monosodium dibasic phosphate | 0.06 | 0.06 | 0.06 | 0.06 | — |
| Tribasic sodium phosphate | — | — | — | — | 0.11 |
| Sodium saccharin | — | 0.15 | 0.15 | 0.15 | 0.15 |
| Sodium benzoate | — | 0.30 | 0.30 | 0.30 | 0.30 |
| AVICEL® RC591 (Microcrystalline cellulose and sodium carboxymethylcellulose) | 0.88 | 0.88 | 0.88 | — | 1.75 |

-continued

| Example | Quantity (% w/w) | | | | |
|---|---|---|---|---|---|
| | 2 | 3 | 4 | 5 | 6 |
| Silicon dioxide | — | 6.25 | 6.25 | 6.25 | 6.25 |
| Propylene glycol alginate | — | — | — | 1.75 | — |
| Gellan gum | — | — | — | — | 0.3 |
| Banana flavor/Cherry flavor | 0.16 | 0.16 | 0.16 | 0.16 | 0.16 |

Procedure:

1. Eslicarbazepine acetate and sucrose were mixed.
2. Tribasic sodium phosphate/sodium saccharin/sodium benzoate/Polysorbate 80 were dissolved in water.
3. The mixture of step 1 was granulated with solution of step 2.
4. The wet mass of step 3 was dried and milled to form granules.
5. Remaining excipients were added to the granules of step 4 and mixed.

The suspension powder for reconstitution is reconstituted with a suitable carrier when required.

Assay for Eslicarbazepine

The suspension powder for reconstitution of Example 1, 2 and 6 were analyzed for drug content by HPLC method using C18 column (150×4.6 mm, 5μρ) using acetonitrile:water (50:50) at 215 nm and the results are provided in Table 1.

TABLE 1

| Assay for Eslicarbazepine | |
|---|---|
| Composition | % Assay |
| Example 1 | 102.9 |
| Example 2 | 99.7 |
| Example 6 | 101.70 | pH data: pH values were determined using potentiometry using USP <791> and the results are provided in Table 2

TABLE 2

| pH Value | |
|---|---|
| Composition | pH |
| Example 1 | 5.40 |
| Example 2 | 5.20 |
| Example 3 | 4.83 |
| Example 4 | 5.43 |
| Example 5 | 4.72 |
| Example 6 | 7.80 |

Dissolution Studies

The powder for suspension of Examples 1-6 were evaluated for in-vitro eslicarbazepine release. The in-vitro dissolution was determined using a USP type 11 apparatus at 100 rpm in 1000 mL of acetate buffer (pH 4.5) at 37±0.5° C. by HPLC method. The results are represented in Table 3.

TABLE 3

Percentage (%) of the In-Vitro Eslicarbazepine Release in USP type II apparatus at 100 rpm in 1000 mL of acetate buffer (pH 4.5)
Percentage of Eslicarbazepine Release

| Time (minutes) | Example 1 | Example 2 | Example 3 | Example 4 | Example 5 | Example 6 |
|---|---|---|---|---|---|---|
| 15 | 102 | 72 | 107 | 110 | 103 | 96 |
| 30 | 101 | 84 | 109 | — | 104 | 98 |
| 45 | 100 | 89 | 109 | — | 104 | 99 |

We claim:

1. An immediate release, liquid oral pharmaceutical suspension dosage form consisting of:
   (a) eslicarbazepine or its pharmaceutically acceptable salt, ester, hydrate or polymorph thereof from about 0.1% to about 10% w/w;
   (b) a suspending agent selected from the group consisting of carboxymethylcellulose, microcrystalline cellulose and a mixture thereof from about 0.89% to about 5% w/w;
   (c) a surfactant selected from poloxamer and polyoxyethylene sorbitan fatty acid ester from about 0.01% to about 3% w/w;
   (d) at least one preservative selected from parabens and their salts present from about 0.001% to about 3% w/w;
   (e) at least one pH adjusting agent selected from citric acid, citrate buffer, and monosodium dibasic phosphate;
   (f) at least one sweetening agent,
   (g) at least one flavoring agent; and
   (h) a pharmaceutically acceptable liquid carrier comprising about 10% w/w glycerin and about 65% to about 89% w/w water;
   wherein the pH of the dosage form is from 3.5 to 5.5 and the dosage form is free of xanthan gum and/or polyoxyethylene stearate.

2. The immediate release liquid oral pharmaceutical suspension dosage form of claim 1, wherein the dosage form exhibits an in-vitro dissolution rate of more than 65% of drug release within 20 minutes, when said dosage form is placed in a dissolution vessel filled with 1000 ml of acetate buffer, pH 4.5 maintained at 37±0.5° C. and stirred at a paddle speed of 100 rpm using a USP Type II (paddle) apparatus.

3. The immediate release, liquid oral pharmaceutical suspension dosage form of claim 1, wherein the pharmaceutically acceptable salt of eslicarbazepine is eslicarbazepine acetate.

4. The immediate release, liquid oral pharmaceutical suspension dosage form of claim 1, wherein the suspension dosage form is free of xanthan gum and polyoxyethylene stearate.

5. The immediate release, liquid oral pharmaceutical suspension dosage form of claim 1, wherein the amount of eslicarbazepine is from about 0.1 mg/ml to about 200 mg/ml and viscosity is from 700 to 1200 cps.

6. The immediate release, liquid oral pharmaceutical suspension dosage form of claim 1, wherein the eslicarbazepine has a particle size distribution $D_{90}$ between 5 μm and 200 μm.

7. A kit comprising:
   (a) an immediate release ready to use suspension dosage form of claim 1;
   (b) a dispensing and/or dosing syringe or a measuring cup for administering the composition; and
   (c) optionally, instructions for preparation and use.

8. An immediate release, ready to use oral pharmaceutical suspension dosage form comprising:
 (a) eslicarbazepine acetate present at from about 0.1% to about 12.5% w/w;
 (b) a suspending agent selected from a mixture of carboxymethylcellulose and microcrystalline cellulose and present at from about 0.05% to about 1.75% w/w;
 (c) a surfactant selected from poloxamer and polyoxyethylene sorbitan fatty acid ester and present at from about 0.01% to about 3% w/w; and
 (d) a liquid carrier comprising about 10% w/w glycerin and about 65% to about 89% w/w water,
 wherein the eslicarbazepine acetate is present in an amount of 0.1 mg/ml to 200 mg/ml, the pH of the suspension is from 3.5 to 5.5, the viscosity of the suspension is from 700 to 1200 cps, and the suspension is free of xanthan gum and/or polyoxyethylene stearate.

9. The immediate release, ready to use, oral pharmaceutical suspension dosage form of claim 8, wherein the dosage form further comprises one or more of an antifoaming agent and a coloring agent.

10. The immediate release, ready to use oral pharmaceutical suspension dosage form of claim 8, wherein the eslicarbazepine has a particle size distribution $D_{90}$ between 5 µm and 200 µm.

11. A ready to use oral pharmaceutical suspension dosage form consisting of:
 (a) eslicarbazepine acetate;
 (b) a mixture of carboxymethylcellulose and microcrystalline cellulose;
 (c) a surfactant selected from poloxamer and polyoxyethylene sorbitan fatty acid ester;
 (d) at least one preservative selected from parabens and their salts;
 (e) at least one pH adjusting agent present in an amount to adjust the pH to be in the range of 3.5 to 5.5;
 (f) at least one sweetening agent,
 (g) at least one flavoring agent; and
 a pharmaceutically acceptable liquid carrier consisting of water and about 10% w/w glycerin.

12. The ready to use oral pharmaceutical suspension dosage form of claim 11, wherein:
 (a) the eslicarbazepine acetate is present at about 5 to about 10% w/w;
 (b) the mixture of carboxymethylcellulose and microcrystalline cellulose is present at about 1.25 to about 2.5% w/w;
 (c) the surfactant is polyoxyethylene sorbitan fatty acid ester;
 (d) the at least one pH adjusting agent is selected from the group consisting of citric acid, citrate buffer, and monosodium dibasic phosphate; and
 (e) the at least one sweetening agent is sorbitol present at about 10 to 20% w/w.

13. The ready to use oral pharmaceutical suspension dosage form of claim 11, wherein the eslicarbazepine is present in an amount of 0.1 mg/ml to 200 mg/ml.

14. The ready to use oral pharmaceutical suspension dosage form of claim 11, wherein the viscosity of the suspension is from 700 to 1200 cps.

15. The ready to use oral pharmaceutical suspension dosage form of claim 11, wherein the eslicarbazepine acetate has a particle size distribution $D_{90}$ between 5 µm and 200 µm.

16. The immediate release, ready to use oral pharmaceutical suspension dosage form of claim 11, wherein:
 (a) eslicarbazepine acetate present at from about 0.1% to about 12.5% w/w;
 (b) the mixture of carboxymethylcellulose and microcrystalline cellulose present at from about 0.05% to about 1.75% w/w; and
 (c) the surfactant present at from about 0.01% to about 3% w/w.

17. A method of treating partial onset seizures in a patient, the method comprising administering the immediate release, liquid oral pharmaceutical suspension dosage form of claim 1.

18. A method of treating partial onset seizures in a patient, the method comprising administering the immediate release, ready to use oral pharmaceutical suspension dosage form of claim 8.

19. A method of treating partial onset seizures in a patient, the method comprising administering the immediate release, ready to use oral pharmaceutical suspension dosage form of claim 11.

* * * * *